(12) United States Patent
Miyashita et al.

(10) Patent No.: US 9,390,826 B2
(45) Date of Patent: Jul. 12, 2016

(54) ENERGY DEGRADER AND CHARGED PARTICLE BEAM IRRADIATION SYSTEM EQUIPPED THEREWITH

(71) Applicant: Sumitomo Heavy Industries, Ltd., Tokyo (JP)

(72) Inventors: Takuya Miyashita, Ehime (JP); Takamasa Ueda, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/607,658

(22) Filed: Jan. 28, 2015

(65) Prior Publication Data
US 2015/0170780 A1 Jun. 18, 2015

Related U.S. Application Data

(63) Continuation-in-part of application No. 14/098,026, filed on Dec. 5, 2013, now abandoned, which is a continuation of application No. PCT/JP2012/056585, filed on Apr. 6, 2012.

(30) Foreign Application Priority Data

Jun. 6, 2011 (JP) .................................. 2011-126342

(51) Int. Cl.
*G21K 1/10* (2006.01)
*A61N 5/10* (2006.01)
(52) U.S. Cl.
CPC ................ *G21K 1/10* (2013.01); *A61N 5/1042* (2013.01); *A61N 2005/1087* (2013.01); *A61N 2005/1095* (2013.01)

(58) Field of Classification Search
USPC ................................. 250/492.3, 505.1, 396 R
See application file for complete search history.

(56) References Cited

U.S. PATENT DOCUMENTS

| 6,034,377 | A | 3/2000 | Pu | |
|---|---|---|---|---|
| 7,456,415 | B2 | 11/2008 | Yanagisawa et al. | |
| 7,755,305 | B2* | 7/2010 | Umezawa | A61N 5/10 250/396 R |
| 2006/0226372 | A1* | 10/2006 | Yanagisawa | A61N 5/10 250/396 R |
| 2009/0161826 | A1* | 6/2009 | Gertner | A61N 5/1017 378/65 |
| 2011/0017920 | A1* | 1/2011 | Goer | A61N 5/10 250/396 R |

FOREIGN PATENT DOCUMENTS

JP 01-286300 A 11/1989
JP 2001-212253 A 8/2001

* cited by examiner

*Primary Examiner* — Phillip A Johnston
*Assistant Examiner* — Hsien Tsai
(74) *Attorney, Agent, or Firm* — Michael Best and Friedrich

(57) ABSTRACT

The present invention provides an energy degrader (10) that can mitigate a reduction in the transmittance of a low-energy charged particle beam, and a charged particle beam irradiation system equipped therewith. The energy degrader includes a plurality of attenuating members (11A to 11G) with different amounts of energy attenuation, and the low-energy-side attenuating member (11G) with a larger amount of energy attenuation is made of a material having a higher transmittance than that of the high-energy-side attenuating member (11A) with a smaller amount of energy attenuation.

6 Claims, 5 Drawing Sheets

US 9,390,826 B2

ENERGY DEGRADER AND CHARGED PARTICLE BEAM IRRADIATION SYSTEM EQUIPPED THEREWITH

INCORPORATION BY REFERENCE

The present application is a continuation-in-part of application Ser. No. 14/098,026 filed Dec. 5, 2013, which is a continuation of Application No. PCT/JP2012/059585 filed on Apr. 6, 2012. The application claims the benefit of Japanese Application No. 2011-126342 filed Jun. 6, 2011. The contents of these three applications, including specification, claims and drawings, are incorporated herein by reference in their entirety.

BACKGROUND

1. Technical Field

The present invention relates to an energy degrader that attenuates the energy of a charged particle beam, and a charged particle beam irradiation system equipped therewith.

2. Description of the Related Art

There are known facilities that irradiate a patient with a charged particle beam, such as a proton beam, to perform cancer treatment. These types of facilities include a cyclotron (accelerator) that accelerates ions (charged particles) generated by an ion source, a transportation line that transports the charged particles accelerated by the cyclotron, and a rotatable irradiation device (rotating gantry) that irradiates a patient with a charged particle beam from arbitrary directions.

A degrader in which a beam absorber (attenuating material) is inserted into a beam line (transportation line) to attenuate beam energy is disclosed in a technique described in the related art.

SUMMARY

According to an embodiment of the present invention, there is provided an energy degrader including a plurality of attenuating members configured to attenuate the energy of an incident charged particle beam, the plurality of attenuating members having different amounts of energy to be attenuated. A low-energy-side attenuating member which is the attenuating member with a larger amount of energy to be attenuated is made of a material having a higher transmittance of the charged particle beam than that of a high-energy-side attenuating member that is the attenuating member with a smaller amount of energy to be attenuated.

DETAILED DESCRIPTION

Figure 1:
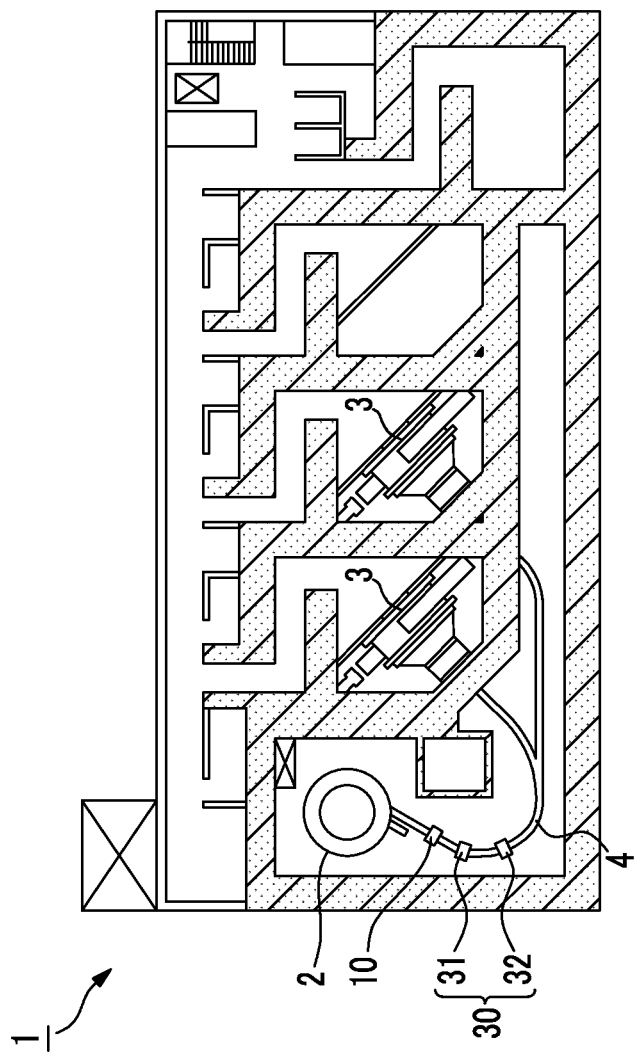
FIG. 1 is an arrangement view of a particle beam treatment system related to an embodiment of the invention.

In charged particle beam irradiation systems of the related art, the energy of the charged particle beam is adjusted based on the irradiation position (depth) of a body to be irradiated. An energy degrader having an attenuating material is used for the adjustment of energy of the charged particle beam. Generally, as the attenuating material, graphite that is not easily radioactivated and is inexpensive is adopted. In the related art, the amount of energy to be attenuated is adjusted by changing a length by which the charged particle beam is transmitted through the attenuating material made of the same material.

Additionally, in recent years, requests for using a charged particle beam having lower energy than usual have been increasing. If the attenuating material is thickened in order to increase the amount of energy attenuation, scattering of the charged particle beam becomes large and the number (=transmittance) of charged particles capable of being transmitted through the attenuating material decreases.

It is desirable to provide an energy degrader that can mitigate a reduction in the transmittance of a low-energy charged particle beam, and a charged particle beam irradiation system equipped therewith.

In the energy degrader related to the embodiment of the invention, the plurality of attenuating members having different amounts of energy attenuation are provided, and the low-energy-side attenuating member with a larger amount of energy attenuation is formed from a material having a higher transmittance than the high-energy-side attenuating member with a smaller amount of energy attenuation. Therefore, a reduction in the transmittance of the low-energy-side proton beam can be mitigated. As a result, in a low energy region (for example, 70 MeV or lower), a reduction in the number of protons that are transmitted through the attenuating members can be suppressed. When the amount of energy attenuation is large, as compared with a case where the amount of energy attenuation is small, the energy of the charged particle beam after being transmitted through the attenuating members becomes low.

Additionally, only the low-energy-side attenuating member with the largest amount of energy to be attenuated among the plurality of attenuating members may be made of a material having a high transmittance. In this way, only the attenuating member with the largest amount of energy attenuation can be made of a material having a higher transmittance compared to the other attenuating members.

Additionally, the low-energy-side attenuating member can be formed from beryllium, and the high-energy-side attenuating member can be formed from graphite. By adopting beryllium as the low-energy-side attenuating member in the aforementioned way, the number of charged particles that are transmitted through the attenuating members can be increased in the low energy region.

Additionally, according to another embodiment of the invention, there is provided a charged particle beam irradiation system that includes the above energy degrader and irradiates the charged particle beam. The charged particle beam irradiation system includes an accelerator configured to accelerate charged particles introduced into the energy degrader; and an irradiation device configured to radiate the charged particle beam having energy attenuated by the energy degrader.

The charged particle beam irradiation system related to the embodiment of the invention includes the energy degrader that attenuates the energy of an incident charged particle beam. In this energy degrader, the plurality of attenuating members having different amounts of energy attenuation are provided, and the low-energy-side attenuating member with a larger amount of energy attenuation is formed from a material having a higher transmittance than the high-energy-side attenuating member with a smaller amount of energy attenuation. Therefore, the transmittance of the low-energy-side charged particle beam can be improved. As a result, in the low energy region, the number of charged particles that are transmitted through the attenuating members can be increased.

According to the energy degrader and the charged particle beam irradiation system equipped therewith of the invention, it is possible to mitigate a reduction in the transmittance of the low-energy charged particle beam and to suppress a reduction in the number of charged particles that is transmitted through the low-energy-side attenuating member.

Hereinafter, preferred embodiments of an energy degrader and a charged particle beam irradiation system equipped therewith related to the invention will be described referring to the drawings. In the present embodiment, a case will be described in which a particle beam treatment system is used as the charged particle beam irradiation system.

Charged Particle Beam Irradiation System

The particle beam treatment system, which is, for example, a device that is used in cancer treatment, irradiates a tumor (target to be irradiated) inside a patient's body with a proton beam (charged particle beam).

As shown in FIG. 1, the particle beam treatment system 1 includes a cyclotron (particle accelerator) 2 that accelerates ions (positive ions of hydrogen) generated in an ion source (not shown) to generate a proton beam, a rotatable rotating gantry (irradiation device) 3 that irradiates a patient with the proton beam from arbitrary directions, and a transportation line 4 that transports the proton beam (charged particle beam accelerated by the cyclotron) generated by the cyclotron 2 to the rotating gantry 3.

The proton beam accelerated by the cyclotron 2 is deflected along the transportation line 4 and transported to the rotating gantry 3. The transportation line 4 is provided with a deflecting electromagnet (not shown) for deflecting the proton beam. Additionally, the transportation line 4 is provided with an energy degrader 10 that attenuates the energy of charged particles (will be described below in detail).

Moreover, an energy selection system (ESS) 30 is provided at a rear stage (downstream) of the energy degrader 10 in the transportation line 4. The ESS 30 selectively takes out a proton beam with a desired energy width, which is a smaller width than a predetermined energy width, from the proton beam with a predetermined energy width that has been transported. In the ESS 30, the energy width of the proton beam is selected so as to fall within a desired range. For example, the ESS 30 selectively takes out a proton beam with an energy width of 190 MeV to 195 MeV in the proton beam with an energy width of 180 MeV to 200 MeV that has been transported from the energy degrader 10 side.

The ESS 30 has a deflecting electromagnet 31 for ESS, and a slit 32. The deflecting electromagnet 31 for ESS is arranged along the transportation line 4, and deflects a proton beam B that forms a magnetic field in the transportation line 4 and travels in the transportation line 4. The deflecting electromagnet 31 for ESS generates a magnetic field so that the proton beam with the aforementioned desired energy width is deflected along the transportation line 4. When the proton beam is deflected by a constant magnetic field, a direction in which the proton beam is deflected changes depending on the energy of the proton beam. By adjusting the magnetic field generated from the deflecting electromagnet 31 for ESS, the proton beam with the aforementioned desired energy width is deflected along the transportation line 4, and the proton beam with the other energy has a larger or smaller direction change than the proton beam along the transportation line 4. As a result, as for the proton beam that has been transported from the energy degrader 10 side, the position of the proton beam within the transportation line 4 changes according to the energy thereof. For example, the deflecting electromagnet 31 for ESS deflects the proton beam with an energy width of 190 MeV to 195 MeV in the proton beam with an energy width of 180 MeV to 200 MeV that has been transported from the upstream side, along the transportation line 4 (along the curvature of the transportation line 4). Additionally, the deflecting electromagnet 31 for ESS greatly deflects the proton beam with an energy width of 180 MeV to 190 MeV further inward than toward the center of the transportation line 4. Moreover, the deflecting electromagnet 31 for ESS deflects the proton beam with an energy width of 195 MeV to 200 MeV at a small angle further outward than toward the center of the transportation line 4.

The slit 32 allows the proton beam with the aforementioned desired energy width to pass therethrough, and shields the proton beam with the other energy. The slit 32 is made of a shielding material that shields a proton beam, and has a hole (not shown) that allows a proton beam to pass therethrough. The slit 32 is arranged so that the hole is located at the center of the transportation line 4. By virtue of such a structure, the slit 32 causes a proton beam with a desired energy width deflected along the transportation line 4 by the deflecting electromagnet 31 for ESS to pass through the hole so as to send the proton beam to the downstream side, and causes the proton beam with the other energy to collide against portions other than the hole so as to shield the proton beam. For example, the slit 32 causes the proton beam with an energy width of 190 MeV to 195 MeV to pass through the hole so as to send the proton beam to the downstream side, and shields the proton beam with the other energy. By virtue of such a function of the deflecting electromagnet 31 for ESS and the slit 32, the ESS 30 can selectively take out a proton beam with a desired energy width, which is a smaller width than a predetermined energy width, from the proton beam with a predetermined energy width that has been transported.

The rotating gantry 3 includes a treatment table on which a patient lies, and an irradiation unit that irradiates the patient with the proton beam. The charged particle beam having energy attenuated by the energy degrader 10 is emitted from the irradiation unit and irradiated to a target region of the patient.

Energy Degrader

Figure 2:
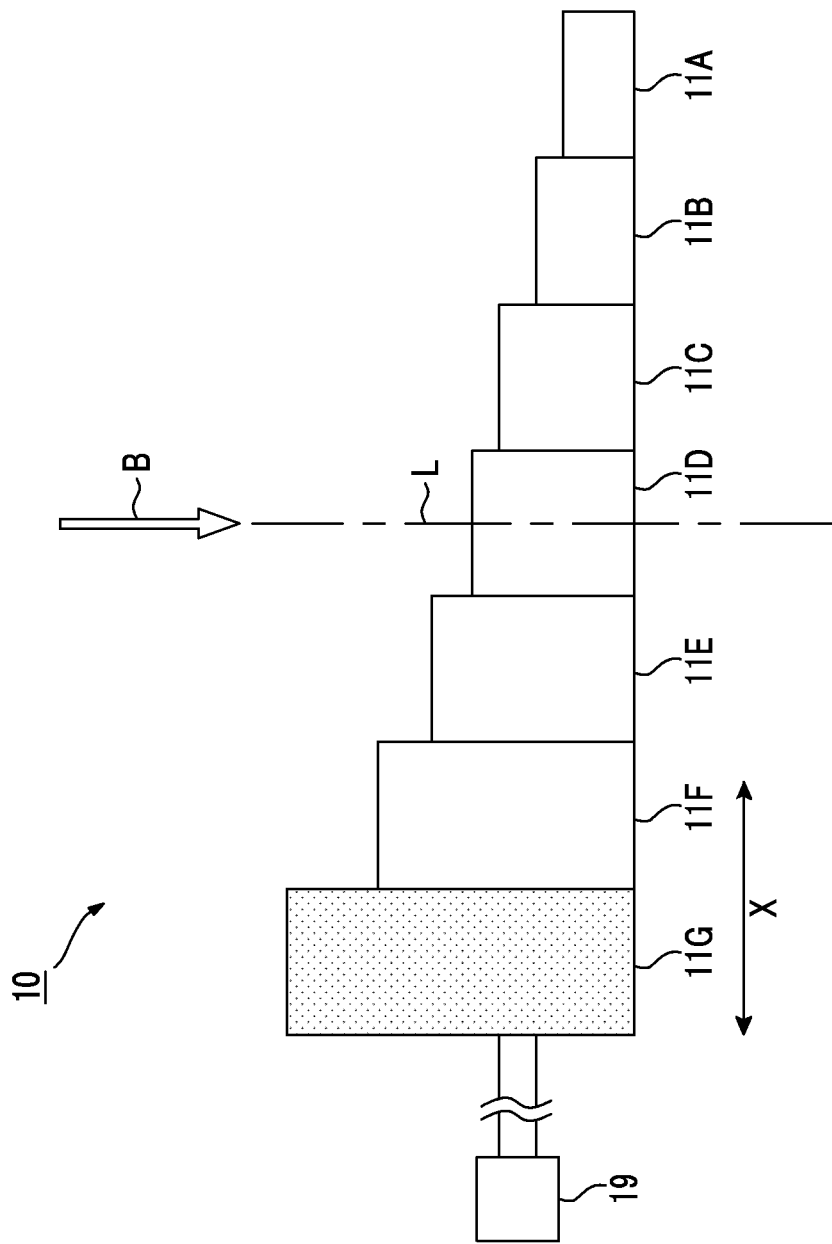
FIG. 2 is a schematic view showing an energy degrader related to the embodiment of the invention.

FIG. 2 is a schematic view showing the energy degrader related to the embodiment of the invention. The energy degrader 10 shown in FIG. 2 is provided on a path L (on a beam line) of a proton beam B to attenuate the energy of the proton beam B. The energy degrader 10 includes a plurality of attenuating members 11A to 11G that attenuate the energy of the proton beam B to be transmitted. The attenuating members 11A to 11G are different from each other in thickness in the traveling direction of the proton beam B, respectively, and the amount of energy attenuation of the proton beam B to be transmitted varies according to the thickness of the attenuating members. In addition, when it is not necessary to distinguish the attenuating members 11A to 11G, these attenuating members are referred to as the attenuating members 11.

In the energy degrader 10, the attenuating members 11 having mutually different thicknesses are arranged in order of thickness in one direction. In the present embodiment, the attenuating members are arranged so as to increase in thickness in order from the attenuating member 11A to the attenuating member 11G in a direction X intersecting the path L of the proton beam B. In addition, the term "thickness" means the length of the charged particle beam in its traveling direction. For example, the attenuating members 11 are arranged so that the end surfaces thereof on an outlet side from which the proton beam B is emitted are aligned, and are arranged so that the end surfaces thereof on an opposite inlet side constitute a stepped shape. In addition, the attenuating members 11 may not be arranged in order of thickness. Additionally, the attenuating members are arranged so that the end surfaces thereof on the outlet side constitute a stepped shape, or may have other arrangements.

The attenuating members 11 are integrally supported by a supporting member (not shown). Additionally, the energy degrader 10 includes a drive unit 19 (for example, a drive motor) that applies a driving force to the attenuating members 11, guide means (for example, a guide rail) for guiding movement of the attenuating members 11, or the like. In the energy degrader 10, the attenuating members 11 are arranged on the path L of the proton beam B depending on a driving force from the drive unit 19, whereby the energy of the proton beam is lowered according to the thickness of the attenuating members 11 through which the proton beam B is transmitted. The attenuating members 11 can greatly lower the energy of the proton beam B to be transmitted as the thickness thereof in the traveling direction of the proton beam B is larger. That is, in the energy degrader shown in FIG. 2, the attenuating member 11A with a smallest thickness has a smallest amount of energy decrease of the proton beam B to be transmitted, and the attenuating member 11G with a largest thickness has a largest amount of energy decrease of the proton beam B to be transmitted.

Some attenuating members among the attenuating members 11A to 11G are formed from materials different from the other attenuating members. Specifically, at least the attenuating member 11G with the largest thickness among the attenuating members 11A to 11G is formed from a material different from the attenuating member 11A with the smallest thickness. The attenuating member 11G is formed from a material having an attenuation factor equal to or near the attenuation factor of a material that forms the attenuating member 11A and having a transmittance higher than the transmittance of the material that forms the attenuating member 11A. In addition, the attenuation factor means the proportion of a decrease in the energy of the proton beam B when the proton beam B with a certain energy is transmitted through the attenuating members 11. Additionally the transmittance means the maintenance proportion of the radiation dose of the proton beam before and after transmission when the proton beam B with a certain radiation dose is transmitted through the attenuating members 11. That is, the transmittance reaches a value near 100% as a change in the radiation dose of a proton beam is smaller before and after transmission, and the transmittance reaches a value near 0 as a change in the radiation dose of a proton beam is larger before and after transmission.

In the energy degrader 10 of the present embodiment, the attenuating member 11G with the largest thickness is formed from a material having an attenuation factor equal to or near the attenuation factor of materials that form the other attenuating members 11A to 11F and having a transmittance higher than the transmittance of the materials that form the attenuating members 11A to 11F. The materials of the attenuating members 11 include, for example, carbon (C), beryllium (Be), or the like. In the present embodiment, beryllium which is a stable solid substance with a smaller atomic number than the atomic number of carbon (graphite), is adopted for the material of the attenuating member 11G with the largest thickness, and carbon (graphite) is adopted for the other attenuating members 11A to 11F. Since scattering of the proton beam B becomes little as the atomic number of attenuating materials is smaller, a decrease in the number of protons capable of being transmitted can be suppressed. Beryllium has an attenuation factor near the attenuation factor of carbon and has a higher transmittance than the transmittance of carbon.

The following Table 1 shows transmittances at individual levels of energy of the proton beam B when the energy of proton beam B are changed using the attenuating members 11 with different thicknesses. The transmittances in Table 1 are values measured not at the outlet of the energy degrader 10 but at the outlet of the ESS 30 provided closer to the downstream side than the energy degrader 10. All the materials of the attenuating member 11 are graphite. The energy degrader 10 radiates a proton beam B with an energy of 230 MeV.

TABLE 1

| Energy of Proton Beam [MeV] | Transmittance (φ5 mm, 32π) [%] |
|---|---|
| 70 | 0.36 |
| 110 | 1.66 |
| 150 | 5.54 |
| 190 | 17.29 |
| 230 | 46.50 |

According to Table 1, it can be seen that the transmittance reaches a smaller value as the energy of the proton beam B is lower (that is, the thickness of the attenuating members 11 is larger). This is because, the thickness of the attenuating members 11 becomes larger, the degree that the proton beam B is radiated within the attenuating members 11 becomes higher and the amount (radiation dose) of the proton beam B capable of being transmitted decreases. The transmittance in the case of 150 MeV is 5.54, whereas the transmittance in the case of 190 MeV is 17.29 (about ⅓ of the transmittance in the case of 190 MeV). That is, when the proton beam B with an energy of 150 MeV is radiated, the radiation dose of a proton beam radiated per unit time decreases compared to a case where a proton beam with an energy of 190 MeV is radiated. In other words, in order to radiate the proton beam B so as to obtain the total value of target radiation doses using the proton beam B with low energy, irradiation time should be lengthened.

In addition, in Table 1, an example in which the energy of the proton beam B reaches 230 MeV is data when the proton beam B was not irradiated to (transmitted through) the attenuating members 11 by avoiding the attenuating material 11 on the path L of the proton beam B. In the ESS 30, as mentioned above, a portion of the proton beam B is removed (shielded) using the slit 32. Therefore, the transmittance is not 100% but 46.50% even in the example of 230 MeV in which the proton beam B is not irradiated to (transmitted through) the attenuating members 11.

The following Table 2 shows the comparison of the transmittance depending on the materials of the attenuating members 12. Measurement is made in cases where the energy of the proton beam B is 70 [MeV] and beam diameters are φ5 mm and φ2 mm. In addition, even in any of a case where the materials of the attenuating members 11 are carbon and a case where the materials are beryllium, the thicknesses of the attenuating members 11 are the same.

TABLE 2

| Beam Diameter | Transmittance Material: Carbon (φ5 mm, 32π) [%] | Transmittance Material: Beryllium (φ5 mm, 32π) [%] |
|---|---|---|
| φ5 mm | 0.358 | 0.578 |
| φ2 mm | 0.478 | 0.744 |

According to Table 2, when the beam diameter is φ5 mm, the transmittance in cases where the materials are carbon is 0.358%, whereas the transmittance in cases where the materials are beryllium is 0.578%. That is, when the materials are beryllium, the transmittance is 1.6 times as compared to the cases where the materials are graphite. Similarly, even when the beam diameter is φ2 mm, the transmittance is about 1.6 times when the materials are beryllium. It can be seen from this that the transmittance of the proton beam B can be improved if beryllium is used as the materials of the attenuating members 11, as compared with a case where carbon is used.

In the energy degrader 10 of the present embodiment, at least the attenuating member 11G with the largest thickness among the attenuating members 11A to 11G is formed from beryllium having an attenuation factor near the attenuation factor of graphite that forms the attenuating member 11A with the smallest thickness and having a transmittance higher than the transmittance of the graphite. Therefore, the attenuating member 11G can offset or reduce the influence of a reduction in the transmittance of proton beam B caused by a large thickness through an improvement in the transmittance resulting from the beryllium material. That is, even when a proton beam is radiated using the attenuating member 11G with the largest thickness, the irradiation time when a proton beam of a total value of target radiation doses is radiated can be kept from becoming long.

In addition, the attenuating member 11F with the largest thickness next to the attenuating member 11G, the attenuating member 11E with the largest thickness next to the attenuating member 11F, as well as the attenuating member 11G with the largest thickness may also formed from beryllium. That is, the attenuating members 11 formed from beryllium can be the plurality of attenuating members 11 necessary without being limited to the attenuating member 11G with the largest thickness. The irradiation time when a proton beam with some low energy is radiated can be kept from becoming long by forming the plurality of attenuating members 11, of which the thickness becomes smaller in order from the attenuating member 11G with the largest thickness, from beryllium. Since beryllium is expensive as compared to graphite, only the attenuating member 11G with the largest thickness may be formed from beryllium when priority is given to the manufacturing cost of a device.

Operation of Energy Degrader and Particle Beam Treatment System

In the particle beam treatment system 1, the proton beam B is accelerated by the cyclotron 2 and the accelerated proton beam B is introduced into the energy degrader 10. In the energy degrader 10, the attenuating members 11 are driven and moved by driving means, and a desired attenuating member 11 is arranged on the path L of the proton beam B. The proton beam B passed through this attenuating member 11 is decelerated by the attenuating member 11 and the energy thereof is attenuated.

The proton beam B passed through the energy degrader 10 is introduced into the ESS 30. The proton beam B with a desired energy range out of the proton beam B introduced into the ESS 30 is taken out selectively. The proton beam B with a selected energy width is transported by the transportation line 4, is introduced into the rotating gantry 3, and is irradiated to a body to be irradiated. This allows the proton beam B to be radiated so as to reach a predetermined depth position inside the body to be irradiated. When the proton beam B is radiated so as to reach a deep position inside the body to be irradiated, attenuation using the energy degrader 10 is made small, and when the proton beam B is radiated so as to reach a shallow position inside the body to be irradiated (for example, near a body surface), the amount of attenuation is made large by the energy degrader 10. Specifically, when the proton beam B is radiated so as to arrive at a deep position inside a body to be irradiated, the attenuating members 11 are moved by the drive unit 19 so that an attenuating member 11 (for example, attenuating member 11G) with a large thickness is arranged on the path L of the proton beam B. When the proton beam B is radiated so as to arrive at a shallow position inside the body to be irradiated, the attenuating members 11 are moved by the drive unit 19 so that an attenuating member 11 (for example, attenuating member 11B) with a small thickness is arranged on the path L of the proton beam B.

In addition, an irradiation nozzle (not shown) for irradiating a patient with the proton beam B is provided within the rotating gantry 3. When the proton beam B is radiated by a well-known broad beam method, the proton beam B having a desired dose distribution is formed using a scatterer, a collimator, or the like that is provided within the irradiation nozzle. When the proton beam B is radiated by a well-known scanning method, scanning using the proton beam B is performed by a scanning electromagnet provided within the irradiation nozzle so that the proton beam B radiated to an affected part of a patient has a desired dose distribution.

Second Embodiment

Figure 3:
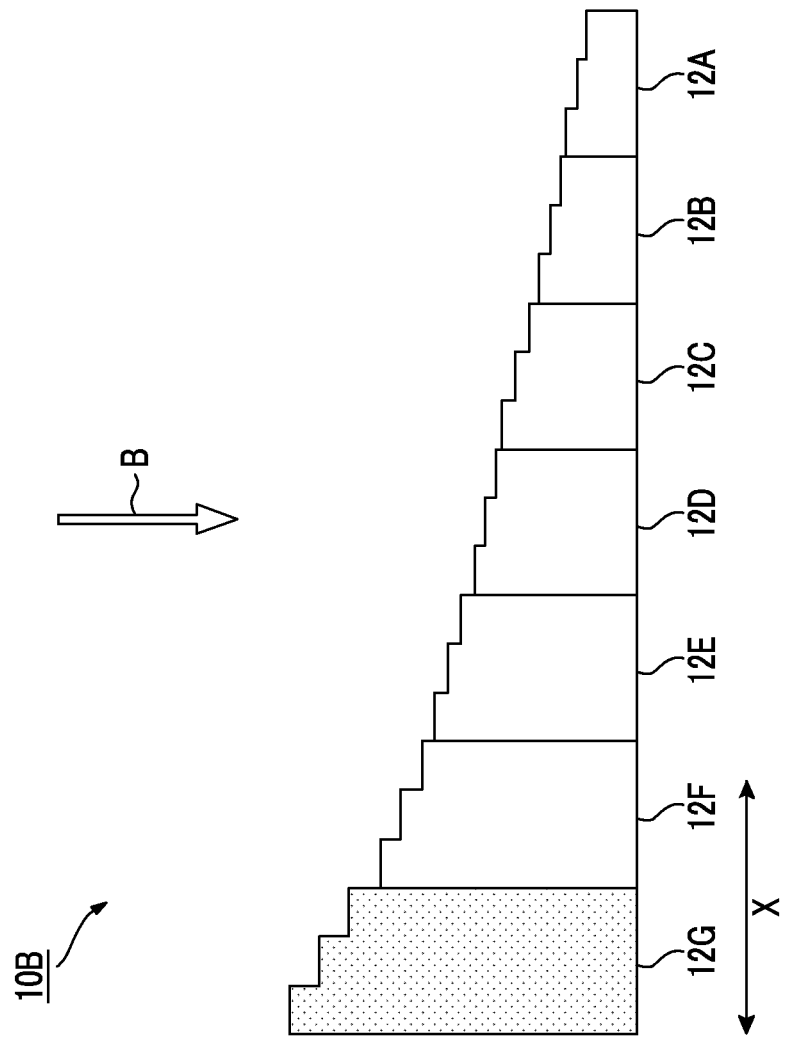
FIG. 3 is a schematic view showing an energy degrader related to a second embodiment of the invention.

Next, an energy degrader 10B related to a second embodiment will be described with reference to FIG. 3. The energy degrader 10B shown in FIG. 3 is different from the energy degrader 10 shown in FIG. 2 in that each of the attenuating members 12A to 12G has a different thickness. In this way, each of the attenuating members 12A to 12G may be configured to have a plurality of thicknesses.

Third Embodiment

Figure 4:
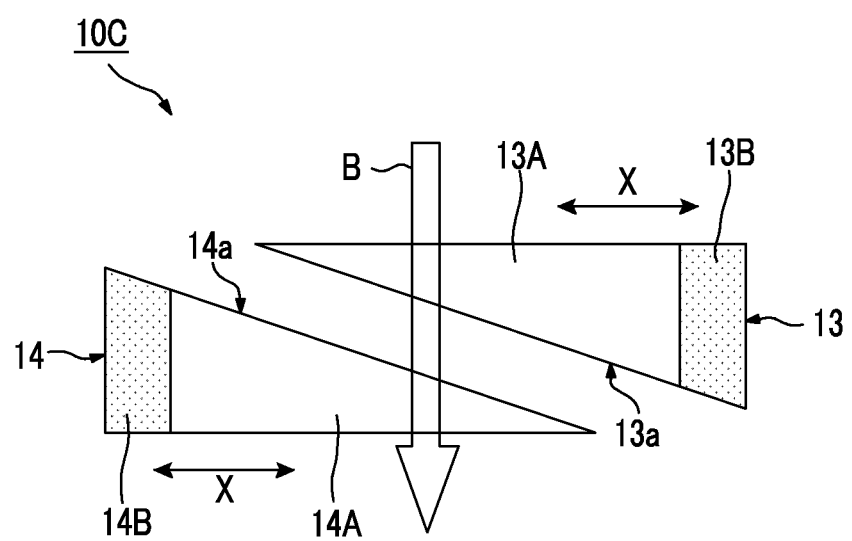
FIG. 4 is a schematic view showing an energy degrader related to a third embodiment of the invention.

Next, an energy degrader 10C related to a third embodiment will be described with reference to FIG. 4. As shown in FIG. 4, the energy degrader 10C has a pair of attenuating members 13 and 14 that are arranged to face each other. The attenuating members 11 form a wedge shape and are arranged such that mutual inclined surfaces 13a and 14a face each other. The attenuating members 13 and 14 are configured so as to be movable in an X direction intersecting a traveling direction of the proton beam B. The amount of energy attenuation of the proton beam B is controlled by moving the attenuating members 13 and 14 in the X direction and changing a length by which the proton beam B is transmitted through the attenuating members 13 and 14. In addition, a configuration may be adopted in which the beam diameter of the proton beam B is controlled by driving any one of the attenuating members 13 and 14 in the traveling direction of the proton beam B to adjust the gap between the attenuating members 13 and 14.

The attenuating members 13 and 14 includes a plurality of attenuating members 13A, 13B, 14A, and 14B having different amounts of energy to be attenuated. Here, the low-energy-side attenuating members 13B and 14B with larger amounts of energy to be attenuated are formed from a material having a higher transmittance of the proton beam B than the high-energy-side attenuating members 13A and 14A with smaller amounts of energy to be attenuated. For example, a material (beryllium) with a high transmittance is adopted only for a portion where the energy of the proton beam B is attenuated to 70 [MeV].

Even in the energy degrader 10C of such a third embodiment, similar to the energy degrader 10 of the above embodiment, in a low energy region, scattering of the proton beam B can be suppressed and a reduction in the number of protons that are transmitted through the attenuating members 13B and 14B can be suppressed.

Fourth Embodiment

Figure 5:
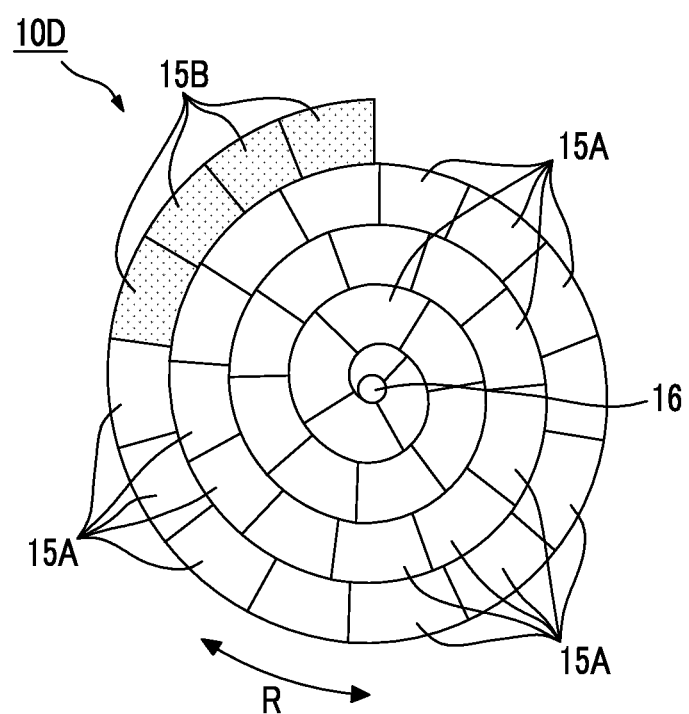
FIG. 5 is a schematic view showing an energy degrader related to a fourth embodiment of the invention.

Next, an energy degrader 10D related to a fourth embodiment will be described with reference to FIG. 5. FIG. 5 is a front view of the energy degrader, and is shown from the traveling direction of the proton beam B. The energy degrader 10D shown in FIG. 5 includes a plurality of attenuating members 15A and 15B having different thicknesses, and the plurality of attenuating members 15A and 15B are arranged spirally. For example, the plurality of attenuating members 15A and 15B are arranged so as to become thin on a central side thereof and become thick on an outer side thereof. For example, the plurality of attenuating members 15A and 15B are arranged so as to become thick on the central side thereof and become thin on the outer side thereof.

A rotating shaft 16 extending parallel to the traveling direction of the proton beam B is arranged at the center of the energy degrader 10D. The rotating shaft 16 is configured so as to be rotatable around an axis and movable in the direction intersecting the traveling direction of the proton beam. As the rotating shaft 16 rotates and moves in a predetermined direction, desired attenuating members 15A and 15B are arranged on the path L of the proton beam.

Here, even in the energy degrader 10D of the fourth embodiment, the low-energy-side attenuating member 15B with a larger amount of energy to be attenuated is formed from a material having a higher transmittance of the proton beam than the high-energy-side attenuating member 15A with a smaller amount of energy to be attenuated. Even in the energy degrader 10D of such a fourth embodiment, similar to the energy degrader 10 of the above embodiment, in a low energy region, scattering of the proton beam B can be suppressed and a reduction in the number of protons that are transmitted through the attenuating members 13B and 14B can be suppressed.

Although the invention has been specifically described above on the basis of the embodiments, the invention is not limited to the above embodiments.

Additionally, the arrangement of the energy degrader 10 is not limited to that immediately after the cyclotron 2, a configuration may be adopted in which the energy degrader 10 is provided in the irradiation nozzle installed at the rotating gantry 3.

Additionally, the accelerator is not limited to the cyclotron 2, and may be, for example, other accelerators, such as a synchro-cyclotron. Additionally, the charged particle beam is not limited to the proton beam, and may be a carbon beam (baryon beam) or the like.

Additionally, the material of the low-energy-side attenuating member is not limited to beryllium, and other attenuating materials may be adopted.

Additionally, the particle treatment system 1 may not use the rotating gantry but may use stationary irradiation.

The energy degrader and the charged particle beam irradiation system equipped therewith of the invention can mitigate a reduction in the transmittance of the low-energy charged particle beam and can suppress a reduction in the number of charged particles that are transmitted through the low-energy-side attenuating member.

What is claimed is:

1. An energy degrader that attenuates the energy of a charged particle beam, the degrader comprising:
   a plurality of attenuating members that are different from each other in thickness in a traveling direction of the charged particle beam, respectively, and are different from each other in the amount of energy attenuation of the charged particle beam according to thickness; and
   a drive unit that drives the attenuating members so that the attenuating members are arranged on a path of the charged particle beam,
   wherein at least an attenuating member with a largest thickness among the plurality of attenuating members is formed from a material having a higher transmittance than a transmittance of the charged particle beam through a material that forms an attenuating member with a smallest thickness.

2. The energy degrader according to claim 1,
   wherein, among the plurality of attenuating members, the attenuating member with the largest thickness is formed from a first material having a higher transmittance than a transmittance of the charged particle beam through a second material that forms the attenuating member with the smallest thickness.

3. The energy degrader according to claim 1,
   wherein at least the attenuating member with the largest thickness among the plurality of attenuating members is formed from beryllium, and the other attenuating members are formed from graphite.

4. A charged particle beam irradiation system including the energy degrader according to claim 1, the system comprising:
   an accelerator that is provided closer to an upstream side than the energy degrader and accelerates charged particles introduced into the energy degrader;
   an irradiation device that irradiates the charged particle beam having energy attenuated by the energy degrader; and
   a transportation line that transports the charged particle beam accelerated by the accelerator up to the irradiation device.

5. The charged particle beam irradiation system according to claim 4, further comprising:
   an energy selection system that is arranged downstream of the energy degrader, and selectively takes out a charged particle beam with a desired energy range, which is a smaller range than a predetermined energy range of the charged particle beam that has been transported from the energy degrader.

6. The charged particle beam irradiation system according to claim 5,
   wherein the energy selection system includes:
   a deflecting electromagnet for ESS that is arranged along the transportation line, and forms a magnetic field in the transportation line to deflect the charged particle beam that advances in the transportation line; and
   a slit that is arranged closer to at the downstream side than the ESS deflecting electromagnet and is made of a shielding material formed with a hole that allows the charged particle beam to pass therethrough.

* * * * *